US007758640B2

(12) United States Patent
Vesely

(10) Patent No.: US 7,758,640 B2
(45) Date of Patent: Jul. 20, 2010

(54) CARDIOVASCULAR VALVE ASSEMBLY

(75) Inventor: Ivan Vesely, Tarzana, CA (US)

(73) Assignee: ValveXchange Inc., Tarzana, CA (US)

( * ) Notice: Subject to any disclaimer, the term of this patent is extended or adjusted under 35 U.S.C. 154(b) by 291 days.

(21) Appl. No.: 11/296,899

(22) Filed: Dec. 8, 2005

(65) Prior Publication Data
US 2006/0136052 A1 Jun. 22, 2006

Related U.S. Application Data

(60) Provisional application No. 60/636,608, filed on Dec. 16, 2004.

(51) Int. Cl.
A61F 2/24 (2006.01)
(52) U.S. Cl. ............ 623/2.38; 623/2.41; 623/2.17
(58) Field of Classification Search .......... 623/2.2, 623/2.36, 2.26, 2.18, 2.17, 2.33, 2.38, 2.41
See application file for complete search history.

(56) References Cited

U.S. PATENT DOCUMENTS

| 3,839,741 | A | * | 10/1974 | Haller | 623/2.34 |
|---|---|---|---|---|---|
| 3,898,701 | A | | 8/1975 | LaRussa | 3/1.5 |
| 4,056,854 | A | | 11/1977 | Boretos et al. | 3/1.5 |
| 4,501,030 | A | | 2/1985 | Lane | 3/1.5 |
| 4,506,394 | A | | 3/1985 | Bédard | 3/1.5 |
| 4,535,483 | A | * | 8/1985 | Klawitter et al. | 623/2.4 |
| 4,680,031 | A | * | 7/1987 | Alonso | 623/2.13 |
| 4,687,483 | A | * | 8/1987 | Fisher et al. | 623/2.14 |
| 4,705,516 | A | * | 11/1987 | Barone et al. | 623/2.39 |
| 4,725,274 | A | * | 2/1988 | Lane et al. | 623/2.18 |
| 4,733,665 | A | | 3/1988 | Palmaz | 604/107 |
| 4,790,843 | A | | 12/1988 | Carpentier et al. | 623/2 |
| 4,851,000 | A | * | 7/1989 | Gupta | 623/2.18 |
| 4,909,789 | A | | 3/1990 | Taguchi et al. | 604/107 |
| 4,917,698 | A | | 4/1990 | Carpentier et al. | 623/2 |
| 5,037,427 | A | | 8/1991 | Harada et al. | 606/108 |
| 5,061,275 | A | | 10/1991 | Wallsten et al. | 623/1 |
| 5,071,431 | A | | 12/1991 | Sauter et al. | 623/2 |
| 5,113,846 | A | | 5/1992 | Hiltebrandt et al. | 600/225 |
| 5,163,953 | A | | 11/1992 | Vince | 623/2 |
| 5,197,978 | A | | 3/1993 | Hess | 623/1.18 |
| 5,312,360 | A | | 5/1994 | Behl | 604/164 |
| 5,411,552 | A | | 5/1995 | Andersen et al. | 623/2 |
| 5,476,510 | A | | 12/1995 | Eberhardt et al. | 623/2.11 |

(Continued)

FOREIGN PATENT DOCUMENTS

WO    WO 9614032 A1 * 5/1996

(Continued)

OTHER PUBLICATIONS

European Search Report for European Patent Application No. 05 027 534.6, Feb. 16, 2006.

(Continued)

Primary Examiner—Paul Prebilic
(74) Attorney, Agent, or Firm—Kusner & Jaffe

(57) ABSTRACT

A cardiovascular valve assembly comprising a base member that is affixed to a patient using conventional sutures or staples, and a replaceable valve member including a valve frame that supports a plurality of valve leaflets. The valve member mates with the base member, and can be detached from the base member for convenient replacement.

24 Claims, 14 Drawing Sheets

U.S. PATENT DOCUMENTS

| | | | | |
|---|---|---|---|---|
| 5,545,214 | A | 8/1996 | Stevens | 623/2 |
| 5,549,665 | A * | 8/1996 | Vesely et al. | 623/2.14 |
| 5,554,185 | A | 9/1996 | Block et al. | 623/2 |
| 5,571,174 | A | 11/1996 | Love et al. | 623/2 |
| 5,593,424 | A | 1/1997 | Northrup, III | 606/232 |
| 5,607,446 | A | 3/1997 | Beehler et al. | 606/198 |
| 5,662,676 | A | 9/1997 | Koninckx | 606/198 |
| 5,718,725 | A | 2/1998 | Sterman et al. | 623/2 |
| 5,755,783 | A | 5/1998 | Stobie et al. | 623/2 |
| 5,807,405 | A | 9/1998 | Vanney et al. | 623/112 |
| 5,840,081 | A | 11/1998 | Andersen et al. | 623/1.11 |
| 5,843,181 | A | 12/1998 | Jaffe et al. | 623/2 |
| 5,855,601 | A | 1/1999 | Bessler et al. | 623/2 |
| 5,910,170 | A * | 6/1999 | Reimink et al. | 623/2.38 |
| 5,928,281 | A * | 7/1999 | Huynh et al. | 623/2.14 |
| 5,957,949 | A | 9/1999 | Leonhardt et al. | 606/194 |
| 5,961,545 | A | 10/1999 | Lentz et al. | 623/1 |
| 5,968,070 | A | 10/1999 | Bley et al. | 606/198 |
| 6,071,263 | A | 6/2000 | Kirkman | 604/104 |
| 6,074,418 | A * | 6/2000 | Buchanan et al. | 623/2.11 |
| 6,106,550 | A | 8/2000 | Magovern et al. | 623/2.38 |
| 6,143,025 | A * | 11/2000 | Stobie et al. | 623/2.39 |
| 6,168,614 | B1 | 1/2001 | Andersen et al. | 623/1 |
| 6,168,616 | B1 | 1/2001 | Brown | 623/1.11 |
| 6,197,054 | B1 | 3/2001 | Hamblin, Jr. et al. | 623/2.38 |
| 6,217,585 | B1 | 4/2001 | Houser et al. | 606/108 |
| 6,249,952 | B1 | 6/2001 | Ding | 29/460 |
| 6,312,465 | B1 | 11/2001 | Griffin et al. | 623/2.38 |
| 6,371,983 | B1 * | 4/2002 | Lane | 623/2.14 |
| 6,454,799 | B1 | 9/2002 | Schreck | 623/2.18 |
| 6,461,382 | B1 | 10/2002 | Cao | 623/2.19 |
| 6,530,952 | B2 | 3/2003 | Vesely | 623/2.18 |
| 6,562,065 | B1 | 5/2003 | Shanley | 623/1.15 |
| 6,569,196 | B1 | 5/2003 | Vesely | 623/2.14 |
| 6,579,305 | B1 | 6/2003 | Lashinski | 623/1.11 |
| 6,663,664 | B1 * | 12/2003 | Pacetti | 623/1.2 |
| 6,733,525 | B2 * | 5/2004 | Yang et al. | 623/2.18 |
| 7,011,681 | B2 | 3/2006 | Vesely | 623/2.11 |
| RE40,377 | E * | 6/2008 | Williamson et al. | 623/2.11 |
| 2001/0002445 | A1 * | 5/2001 | Vesely | 623/2.11 |
| 2002/0055775 | A1 * | 5/2002 | Carpentier et al. | 623/2.17 |
| 2002/0198594 | A1 * | 12/2002 | Schreck | 623/2.11 |
| 2003/0125793 | A1 | 7/2003 | Vesely | 623/1.11 |
| 2004/0030381 | A1 | 2/2004 | Shu | 623/2.11 |
| 2004/0122514 | A1 * | 6/2004 | Fogarty et al. | 623/2.14 |
| 2004/0186563 | A1 * | 9/2004 | Lobbi | 623/2.11 |
| 2004/0186565 | A1 | 9/2004 | Schreck | 623/2.18 |
| 2004/0225356 | A1 | 11/2004 | Frater | 623/2.14 |
| 2005/0075717 | A1 * | 4/2005 | Nguyen et al. | 623/1.26 |
| 2005/0159811 | A1 | 7/2005 | Lane | 623/2.14 |
| 2005/0228494 | A1 * | 10/2005 | Marquez | 623/2.18 |
| 2006/0135964 | A1 | 6/2006 | Vesely | 606/108 |
| 2006/0136052 | A1 | 6/2006 | Vesely | 623/2.18 |
| 2008/0004696 | A1 | 1/2008 | Vesely | 623/2.1 |

FOREIGN PATENT DOCUMENTS

| | | |
|---|---|---|
| WO | 99/33414 | 7/1999 |
| WO | WO 99/53845 A1 * | 10/1999 |
| WO | WO 00/47139 | 8/2000 |
| WO | WO 2006/127756 | 11/2006 |
| WO | WO 2008/051428 | 5/2008 |
| WO | WO 2008/088835 | 7/2008 |

OTHER PUBLICATIONS

European Search Report for European Patent Application No. 01 98 7412.2, Oct. 19, 2006.

U.S. Appl. No. 10/341,049, filed Jan. 13, 2003, Vesely, entitled: Bioprosthetic Cardiovascular Valve System.

U.S. Appl. No. 10/341,049, filed Jan. 13, 2003, Vesely, entitled: Bioprosthetic Cardiovascular Valve System.

European Search Report for European Patent Application No. 07 111 254.4, Aug. 22, 2007.

* cited by examiner

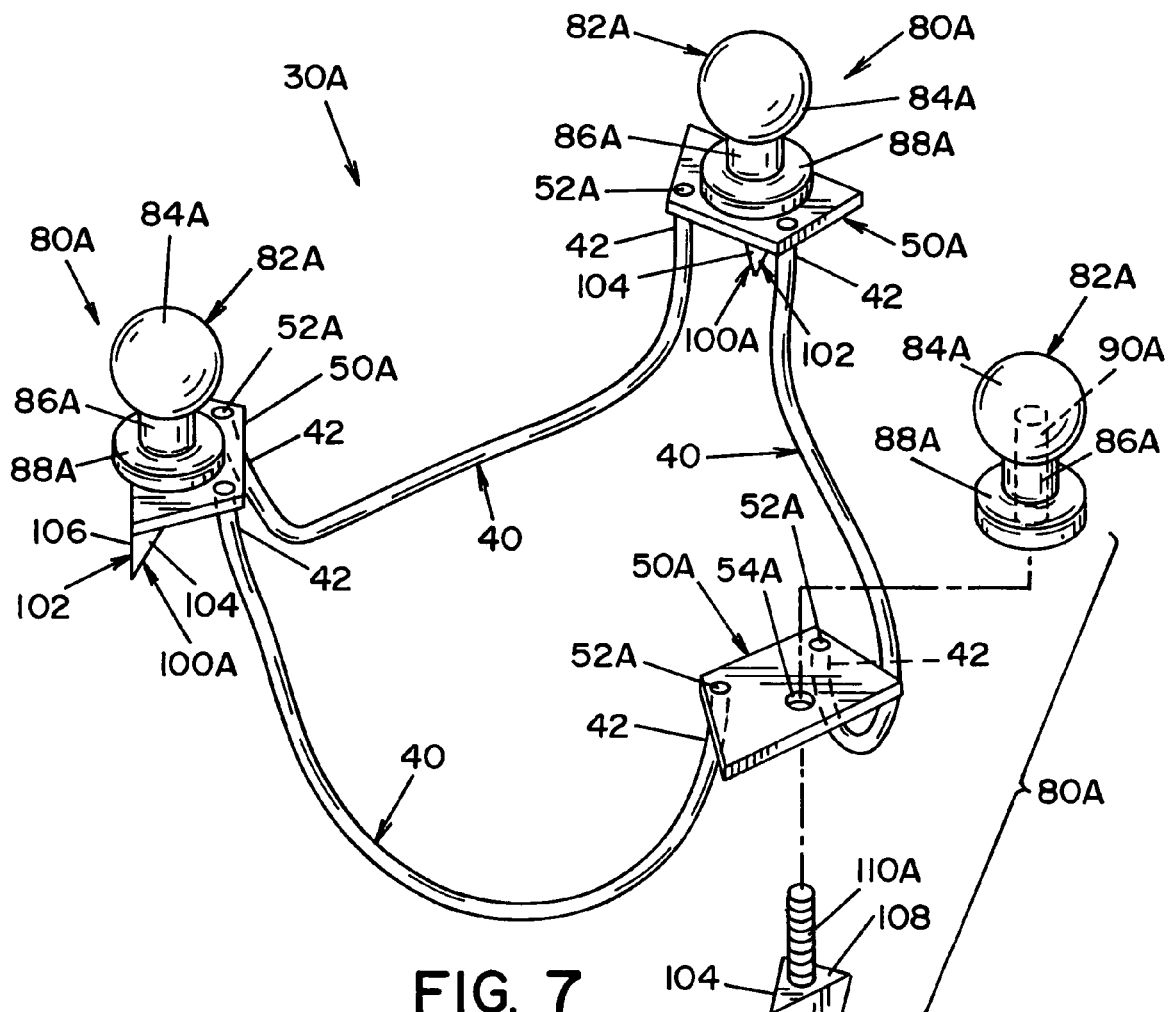
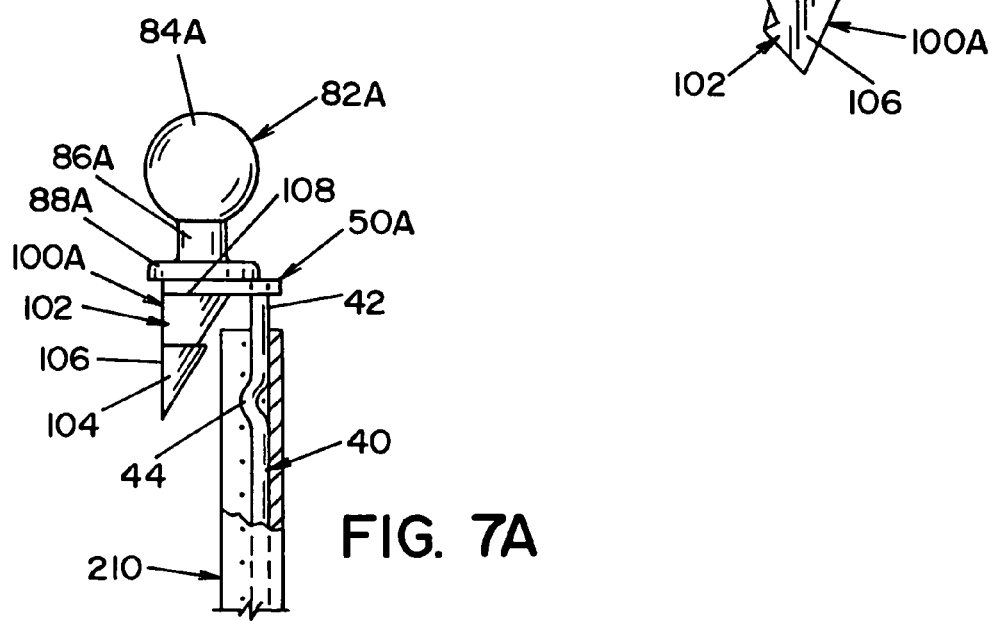
FIG. 7
FIG. 7A

CARDIOVASCULAR VALVE ASSEMBLY

RELATED APPLICATIONS

This application claims the benefit of U.S. Provisional Application No. 60/636,608, filed Dec. 16, 2004, which is hereby fully incorporated herein by reference.

FIELD OF THE INVENTION

The present invention relates generally to a cardiovascular valve assembly, and more specifically relates to a cardiovascular valve assembly comprised of a base member that remains in a patient, and a valve member that is detachably mountable to the base member.

BACKGROUND OF THE INVENTION

The current practice of inserting a bioprosthetic cardiovascular valve involves cutting a patient's chest open, placing the patient on cardiopulmonary bypass, and surgically inserting the valve into an aorta. This process can take several hours and subjects the patient to significant operative mortality. While operative mortality during a first valve replacement surgery can be very low, subsequent valve replacement surgeries have increased operative mortality. Consequently, first and second re-operations to replace a worn out cardiovascular valve are usually avoided. However, since many typical cardiovascular valves have a lifespan of about 10 years, it often becomes necessary to replace cardiovascular valves one or more times.

One goal of bioprosthetic cardiovascular valve research has been to improve the durability of cardiovascular valves, so that the valves can be put into patients only once, and will last the life of the patient. Thus far, this goal has been extremely difficult to reach.

The present invention addresses deficiencies in the durability of cardiovascular valves by providing a cardiovascular valve that can be easily inserted for initial installation, easily removed when the valve begins to fail, and easily re-inserted for valve replacement. Advances in the field of catheter-based end vascular procedures, and more broadly, the field of Minimally Invasive Surgery (MIS), facilitate procedures for insertion and removal of cardiovascular valves according to the present invention.

SUMMARY OF THE INVENTION

In accordance with the present invention, there is provided a cardiovascular valve assembly comprising: (a) a base member; and (b) a valve member detachably mountable to the base member, said valve member including: at least one mounting assembly engageable with the base member, and a wireform for supporting leaflets, said wireform connected with each of said at least one mounting assemblies.

An advantage of the present invention is the provision of a cardiovascular valve assembly including a replaceable valve member and a base member, wherein the replaceable valve member is conveniently attachable to and detachable from the base member that can be permanently installed in a patient.

Still another advantage of the present invention is the provision of a cardiovascular valve assembly that comprises a replaceable valve member including a valve frame that is sufficiently elastic to allow expansion and collapse thereof.

Yet another advantage of the present invention is the provision of a cardiovascular valve assembly including a replaceable valve member having a mounting assembly that can be gripped by snares.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein:

FIG. 7 is an exploded view of a valve frame, according to an alternative embodiment;

FIG. 7A is an enlarged partially sectioned view of a wireform according to an alternative embodiment;

DETAILED DESCRIPTION OF THE INVENTION

Figure 1:
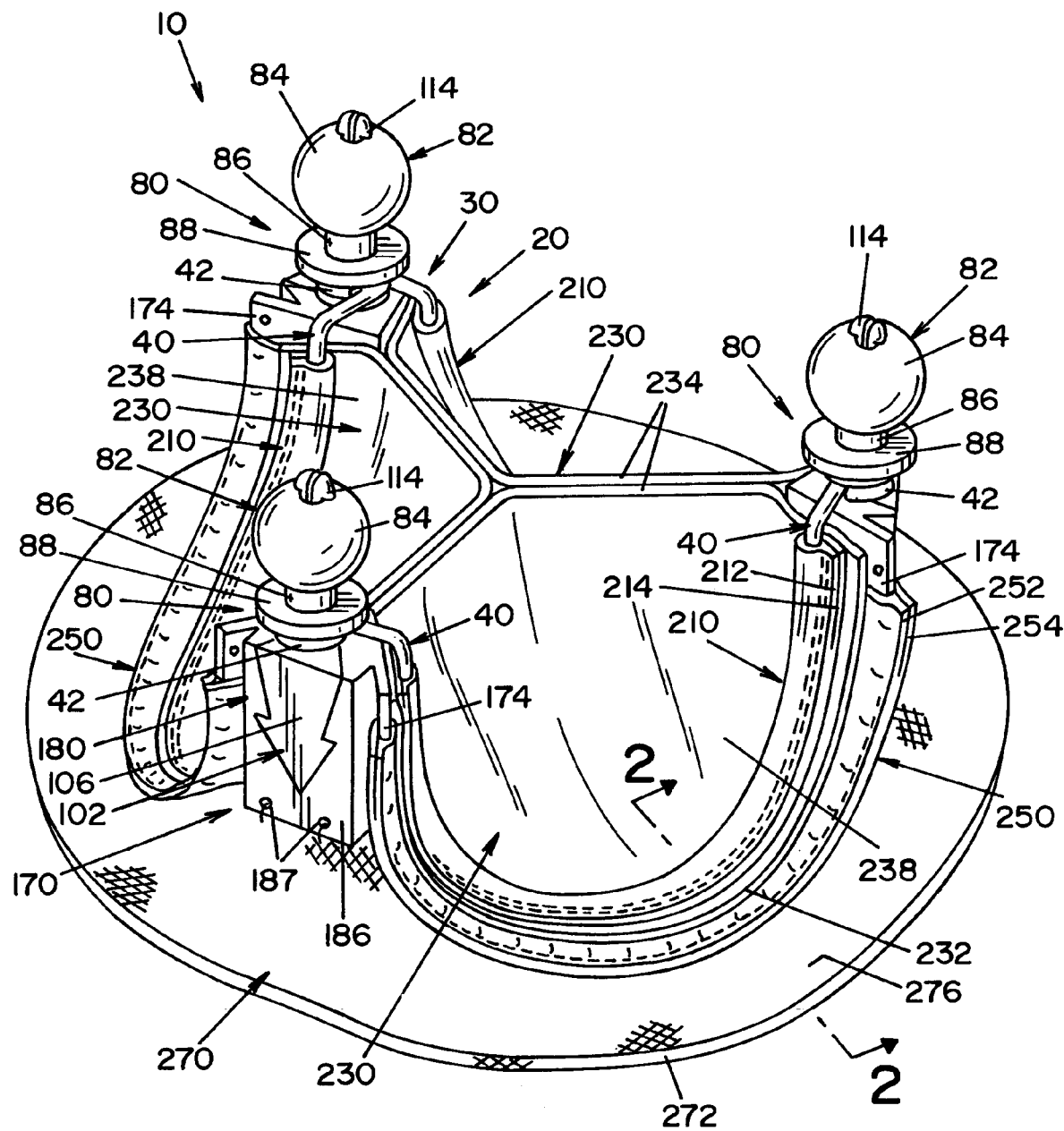
FIG. 1 is a perspective view of a fully assembled cardiovascular valve assembly according to one embodiment of the present invention, the cardiovascular valve assembly including a replaceable valve member and a base member.

The present invention provides improvement to the devices disclosed in U.S. Pat. No. 6,530,952 entitled "Bioprosthetic Cardiovascular Valve System" (issued Mar. 11, 2003) and U.S. Pat. No. 6,569,196 entitled "System for Minimally Invasive Insertion of a Bioprosthetic Heart Valve" (issued May 27, 2003), both of which are fully incorporated herein by reference. Disclosed herein are various embodiments of the present invention. It should be understood that the present invention may be practiced using a combination of features from the various embodiments disclosed herein. In the drawings, similar components of the various embodiments will bear the same reference numbers.

Referring now to the drawings wherein the showings are for the purposes of illustrating embodiments of the present invention only and not for the purposes of limiting same, FIG. 1 illustrates a cardiovascular valve assembly 10 according to one embodiment of the present invention. Cardiovascular valve assembly 10 is basically comprised of a replaceable valve member 20 and a base member 170. Valve member 20 is generally comprised of a valve frame 30 and a plurality of pericardial leaflets 230 mounted thereto. Base member 170 is sewn to a patient using a sewing cuff 270, as will be described in detail below. Replaceable valve member 20 is detachably mountable to base member 170, as will also be described in detail below.

Figure 3:
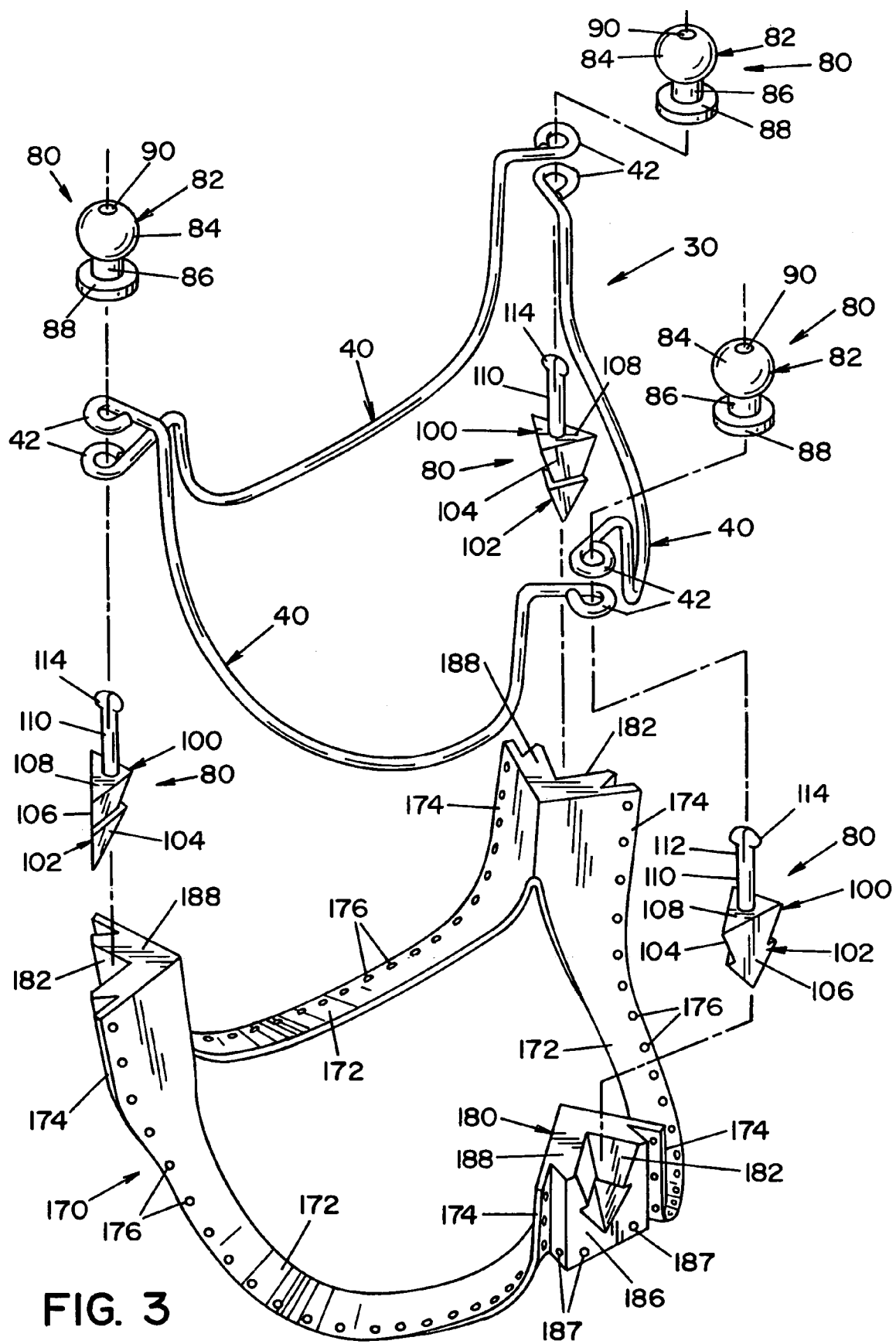
FIG. 3 is an exploded view of the cardiovascular valve assembly of FIG. 1, without valve leaflets and a sewing cuff.
Figure 4:
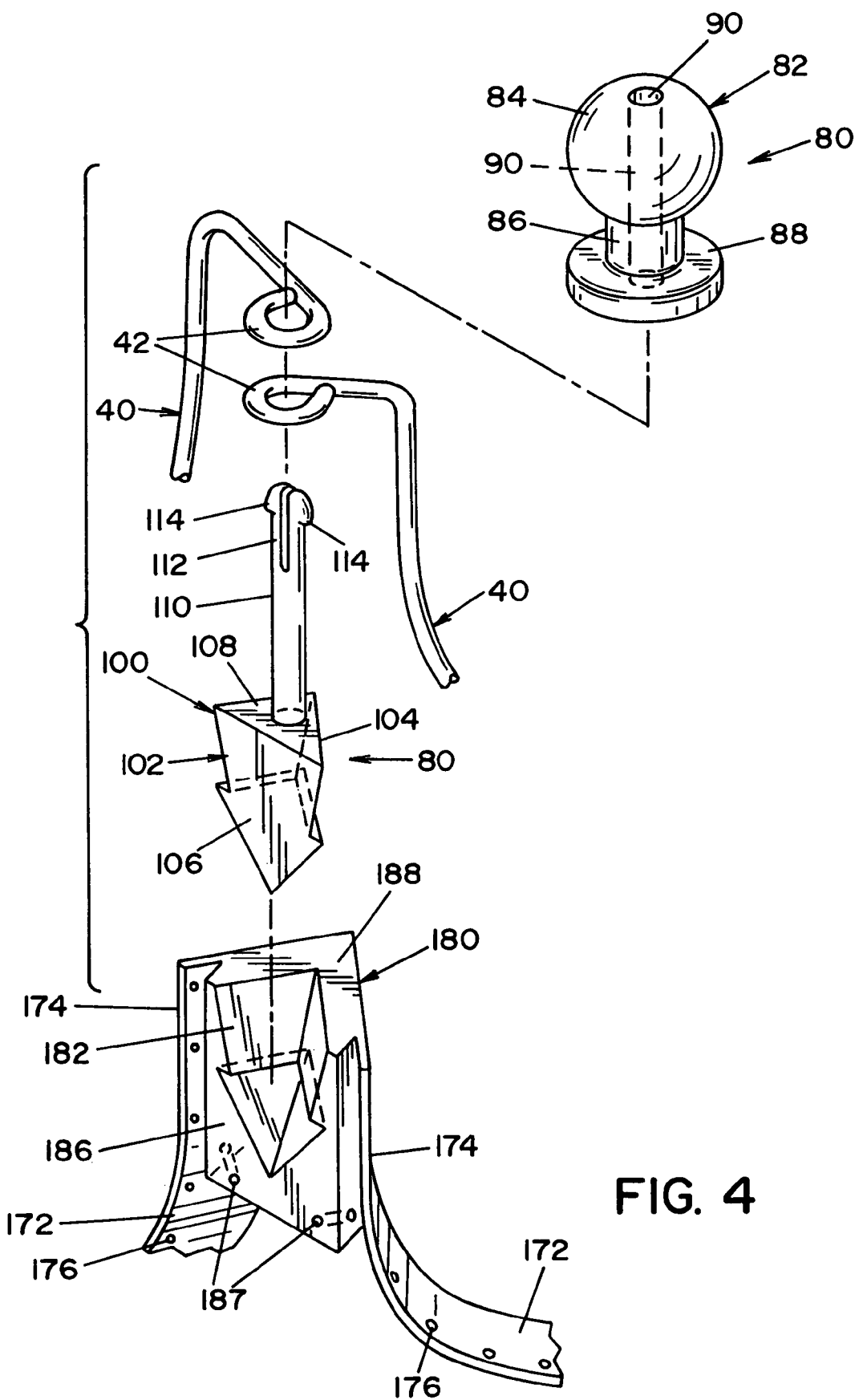
FIG. 4 is an enlarged exploded view of a mounting assembly shown in FIG. 3.

A first embodiment of valve member 20 will now be described in detail with reference to FIGS. 3 and 4. As discussed above, valve member 20 is generally comprised of valve frame 30 and a plurality of pericardial leaflets 230 mounted thereto. Pericardial leaflets 230 are omitted from FIGS. 3 and 4 for improved clarity. Valve frame 30 includes a wireform comprised of a plurality of wireform sections 40, and a mounting assembly 80.

Each wireform section 40 of valve frame 30 has a generally arcuate shape, and has an end portion 42 at distal ends thereof. In the embodiment shown, each end portion 42 is arranged to form a generally circular loop. Wireform sections 40 are preferably made of a medical grade metal wire with suitable elasticity, such as Algiloy, nitinol, stainless steel, platinum, gold, titanium, other biocompatible metals, and combinations thereof. It should be understood that a preferred material for wireform sections 40 has an elasticity such that the material returns to its original shape after being deformed. However, it is contemplated that a material that does not return to its original shape after deformation could also be suitably used.

Mounting assembly 80 is comprised of a cap 82 and a support member 100. In the embodiment shown, cap 82 has a bulbous portion 84, a neck 86 and a base 88. A hole 90 extends through cap 82, as best seen in FIG. 4. Cap 82 is an engagement means for facilitating engagement of mounting assembly 80 with an installation/removal tool, as will be described below.

Support member 100 comprises a retaining pin 110 and a mounting element 102. Retaining pin 110 includes a split end 112 having locking tabs 114 extending therefrom. Split end 112 compresses to allow retaining pin 110 to be inserted into hole 90 of cap 82. Locking tabs 114 extend out through hole 90 and lock cap 82 onto support member 100, as shown in FIG. 1.

Mounting element 102 has an inner face 104, an outer face 106 and a top face 108. In the illustrated embodiment, mounting element 102 takes the form of a prismatic-shaped "spike" with engagement surfaces formed in inner face 104.

Wireform sections 40 are mounted to support member 100 by first mounting end portions 42 of adjacent wireform sections 40 onto retaining pin 110. Thereafter, cap 82 is slid onto retaining pin 110 to capture end portions 42 between base 88 of cap 82 and top face 108 of mounting element 102. As indicated above, locking tabs 114 extend out through hole 90, thereby locking cap 82 onto support member 100.

It should be appreciated that in accordance with an alternative embodiment of the present invention, the wireform may be comprised of a single continuous wireform section that is connected with each support member 100. In this regard, loops may be formed in the single continuous wireform section at appropriate locations for mounting to retaining pins 110. Alternatively, the single continuous wireform section may be connected with the support element by spot welding or other means.

While an illustrated embodiment of the present invention shows three (3) wireform sections 40 and three (3) mounting assemblies 80, it is contemplated that the number of wireform sections 40 and mounting assemblies 80 may be less than or greater than three.

Base member 170 will now be described in detail with reference to FIGS. 3 and 4. Base member 170 is generally comprised of a plurality of arcuate sections 172. Holes 176 are located along the length of each arcuate section 172 for attachment of a base wrap 250, as will be described below. Distal ends 174 of adjacent arcuate sections 172 join a common mounting section 180. Mounting section 180 includes a mating recess 182 dimensioned to receive mounting element 102 of support member 100. Mounting element 102 and mounting section 180 define interlocking surface means. Mounting section 180 has an outer face 186 and an upper face 188. Holes 187 extend through mounting section 180 along the lower end of outer face 186 for attachment of sewing cuff 270 (FIG. 1), as will be described below.

As best seen in FIG. 1, when mounting element 102 is received into mating recess 182, outer surface 106 is generally flush with outer face 186 of mounting section 180 and top face 108 is generally flush with upper face 188.

While an illustrated embodiment shows three (3) arcuate sections 172 and three (3) mounting sections 180, it is contemplated that the number of arcuate sections 172 and mounting sections 180 may be less than or greater than three.

Figure 5:
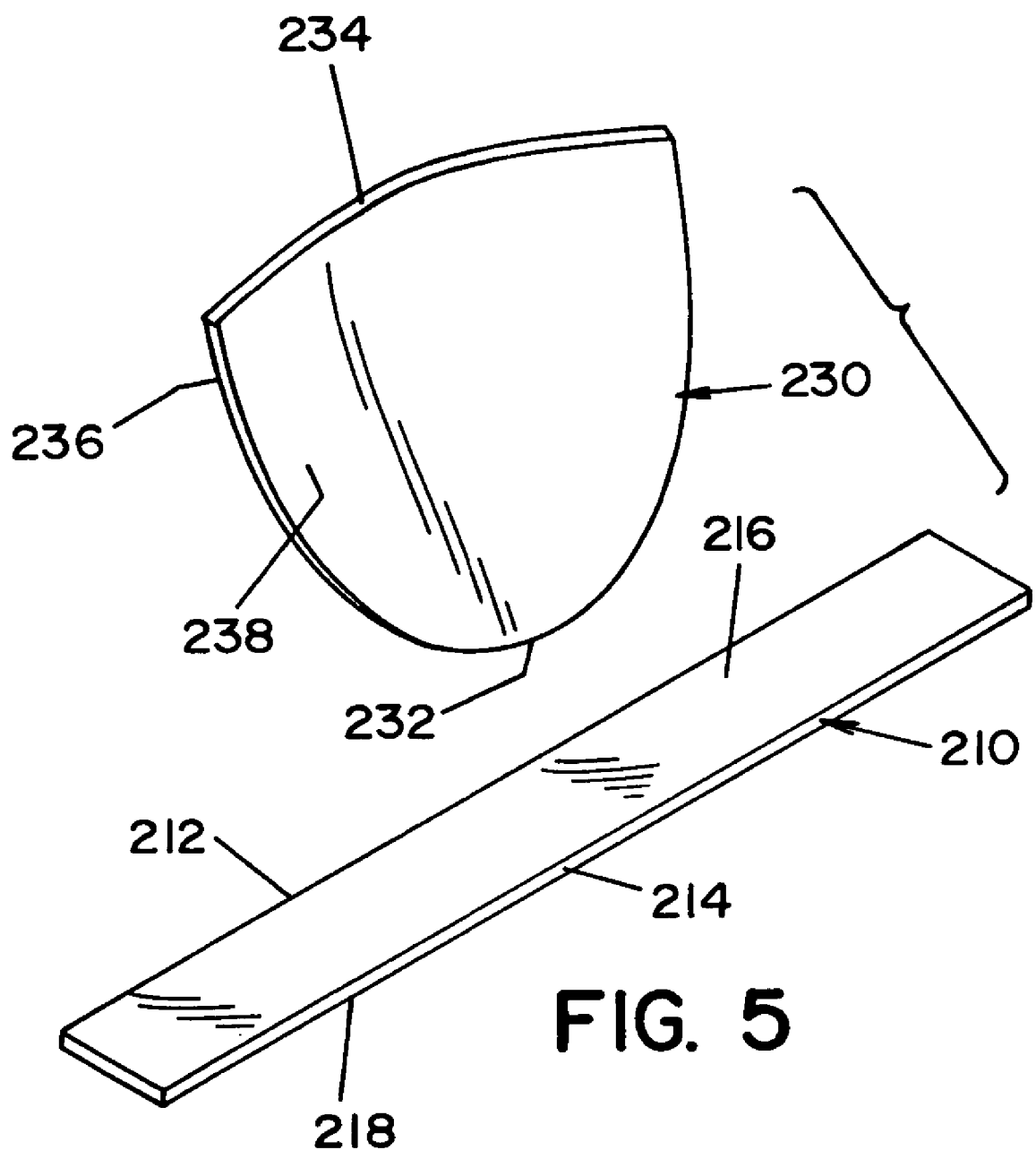
FIG. 5 shows a valve leaflet and an associated frame wrap member.

Attachment of pericardial leaflets 230 to wireform sections 40 will now be described with reference to FIGS. 1, 2 and 5. With particular reference to FIG. 5, there is shown a pericardial leaflet 230 and a frame wrap 210. Leaflet 230 has a first end 232 and a second end 234. First end 232 is fixed relative to valve frame 30, as will be described below. Second end 234 of leaflet 230 is free to move during ordinary operation of valve member 20. Leaflet 230 also has an inner surface 236 and an outer surface 238. In the illustrated embodiment, a frame wrap 210 is used to attach each leaflet 230 to wireform sections 40, as will be described below. Frame wrap 210 has a first edge 212, a second edge 214, an inner surface 216, and an outer surface 218. Leaflet 230 and frame wrap 210 are preferably made of a biocompatible, non-thrombogenic material, such as glutaraldehyde-fixed pericardium of bovine, porcine, equine or any other human or animal origin.

Figure 2:
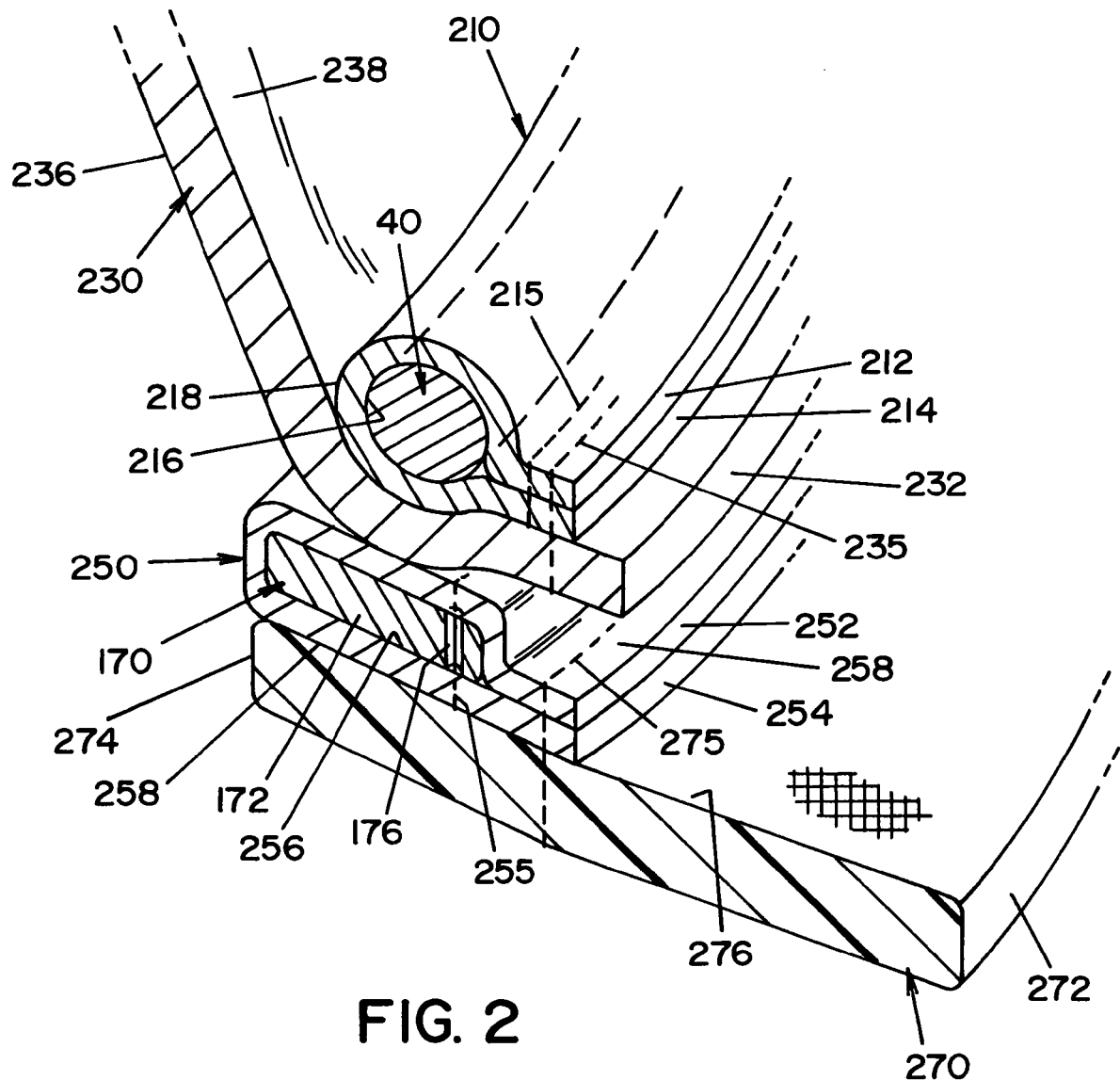
FIG. 2 is a cross-sectional view of the cardiovascular valve assembly of FIG. 1, taken along lines 2-2.

Referring now to FIG. 2, pericardial leaflets 230 are attached to wireform sections 40 by attachment to frame wrap 210. In this regard, frame wrap 210 is first wrapped around each wireform section 40, wherein first edge 212 is joined to second edge 214. First edge 212 is stitched to second edge 214 generally along line 215 to capture wireform section 40, thereby permanently attaching frame wrap 210 to valve frame 30. Outer surface 238 of leaflet 230 is then located adjacent to outer surface 218 of frame wrap 210. First end 232 is stitched to frame wrap 210 generally along line 235, thereby permanently attaching leaflet 230 to frame wrap 210. In a preferred embodiment, end 232 of leaflet 230 extends beyond edges 212, 214 of frame wrap 210 (e.g., by 1-5 mm) to impede displacement of frame wrap 210 along the length of wireform section 40. Furthermore, extension of ends 232 beyond edges 212, 214 of frame wrap 210 allows leaflets 230 to cover any gap that may exist between valve frame 30 and base member 170 when valve member 20 is fully installed in base member 170. As a result, blood leakage between valve member 20 and base member 170 is prevented.

Figure 6:
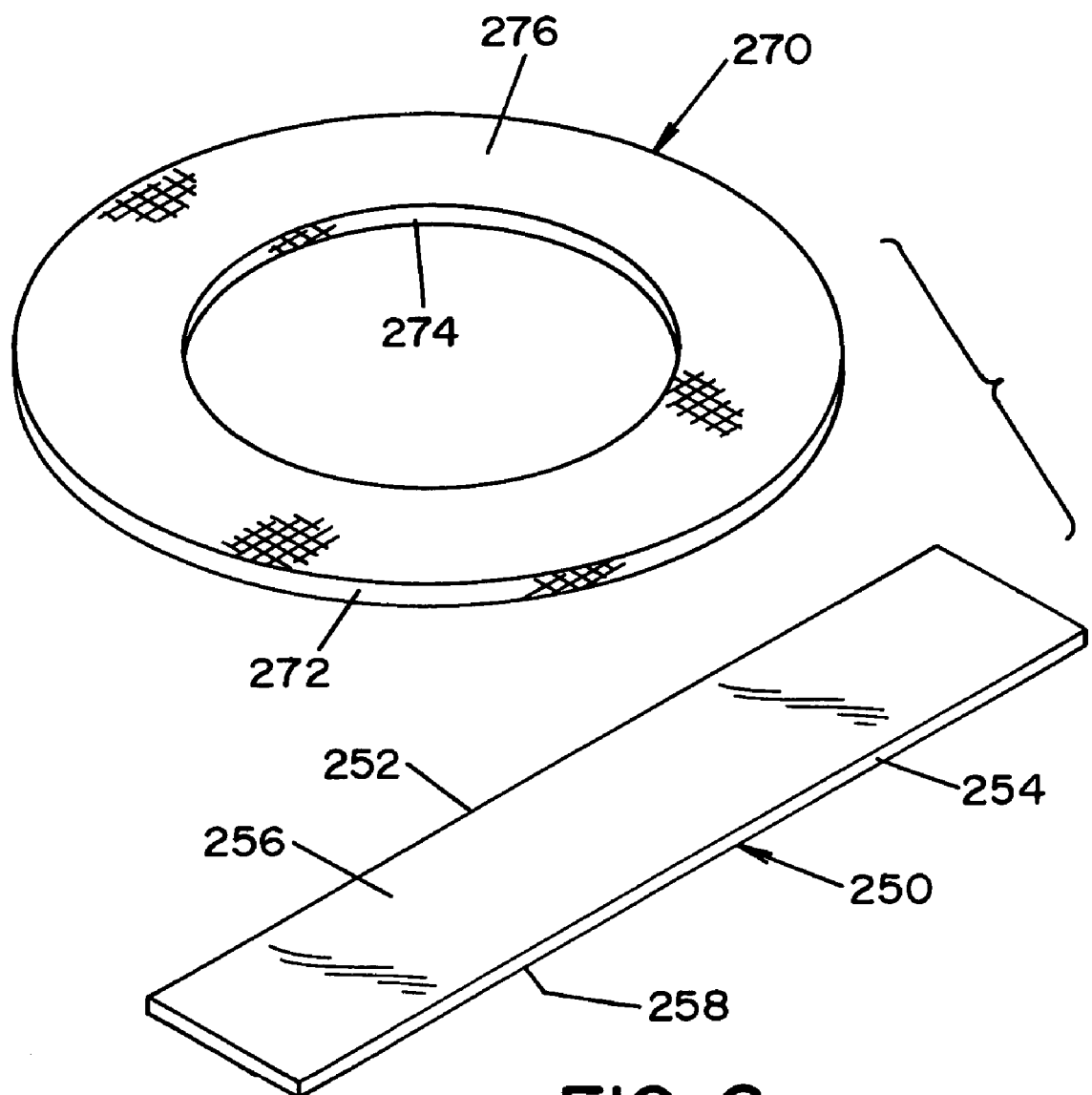
FIG. 6 shows a sewing cuff and an associated base wrap member.

Attachment of sewing cuff 270 to base member 170 will now be described with reference to FIGS. 1, 2 and 6. Sewing cuff 270 is provided to attach base member 170 to body tissue inside a patient. With particular reference to FIG. 6, there is shown sewing cuff 270 and a base wrap 250. Sewing cuff 270 preferably takes the form of a ring having an outer edge 272 and an inner edge 274. Sewing cuff 270 also has an upper surface 276. Base wrap 250 is attached to each arcuate section 172 of base member 170 to attach sewing cuff 270 to base member 170, as will be described below. Base wrap 250 has a first edge 252, a second edge 254, an inner surface 256, and an outer surface 258. Sewing cuff 270 and base wrap 250 are preferably made of Dacron or other medical grade cloth.

With further reference to FIG. 2, sewing cuff 270 is attached to base member 170 using base wrap 250. In this regard, each base wrap 250 is wrapped around an arcuate section 172 of base member 170. First edge 252 is stitched to second edge 254 generally along line 255 to capture each arcuate section 172, thereby permanently attaching base wrap 250 to base member 170. Holes 176 located along the length of arcuate sections 172 may be used to directly stitch base wrap 250 to base member 170. Upper surface 276 of sewing cuff 270 is located adjacent to outer surface 258 of base wrap 250, as shown in FIG. 2. Sewing cuff 270 is stitched to base wrap 250 generally along line 275, thereby permanently attaching sewing cuff 270 to base member 170. In the illustrated embodiment, outer edge 272 of sewing cuff 270 extends outward from arcuate sections 172 of base member 170. Holes 187 of mounting sections 180 may be used to stitch sewing cuff 270 directly to base member 170.

Referring now to FIG. 7, there is shown an alternative valve frame 30A. In this embodiment, a mounting assembly 80A is comprised of a plate 50A, a cap 82A, and a support member 100A. Plate 50A is generally planar, and includes recesses 52A and a hole 54A. Recesses 52A are dimensioned to receive end portions 42 of wireform sections 40. In the illustrated embodiment, end portions 42 are inserted into recesses 52A and spot welded to plate 50A. Accordingly, adjacent end portions 42 of wireform sections 40 are joined to a common plate 50A. Hole 54A is dimensioned to receive a threaded retaining pin 110A, described below. Cap 82A has a bulbous portion 84A, a neck 86A and a base 88A. A threaded recess 90A extends into cap 82A from base 88A. Support member 100A is comprised of threaded retaining pin 110A and a mounting element 102. Threaded retaining pin 110A is dimensioned to threadingly engage with threaded hole 90A. Mounting element 102 has been described in detail above.

With regard to assembly of mounting assembly 80A, retaining pin 110A is inserted through hole 54A of plate 50A, and cap 82A is then threaded onto retaining pin 110A. Accordingly, plate 50A is captured between base 88A of cap 82A and top face 108 of mounting element 102.

Referring now to FIG. 7A, there is shown an alternative embodiment of wireform sections 40. In this embodiment, a kink or bend 44 is located in wireform sections 40 proximate to end portion 42. Kink or bend 44 helps to prevent slippage or dislocation of frame wrap member 210 along wireform section 40.

Figure 8:
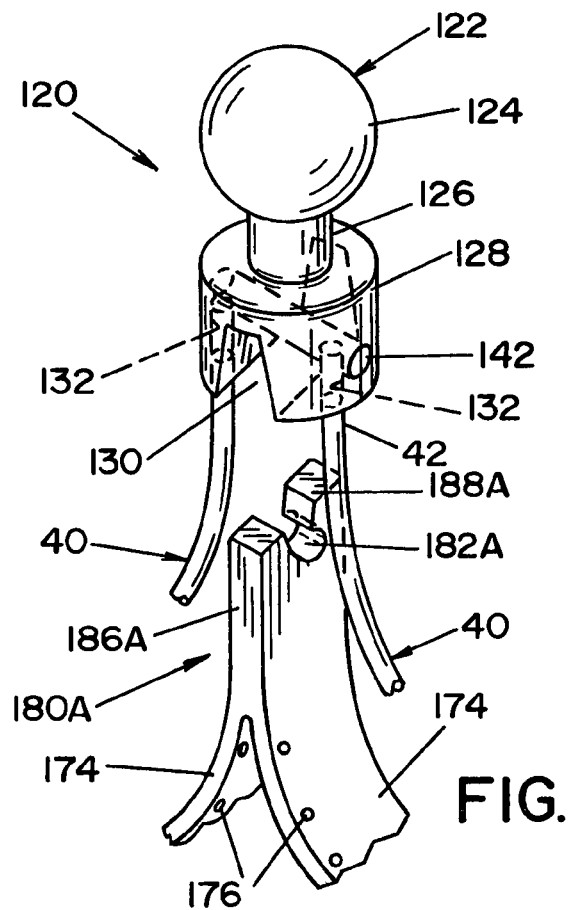
FIG. 8 is a perspective view of a mounting assembly and a corresponding mounting section, according to an alternative embodiment.
Figure 9:
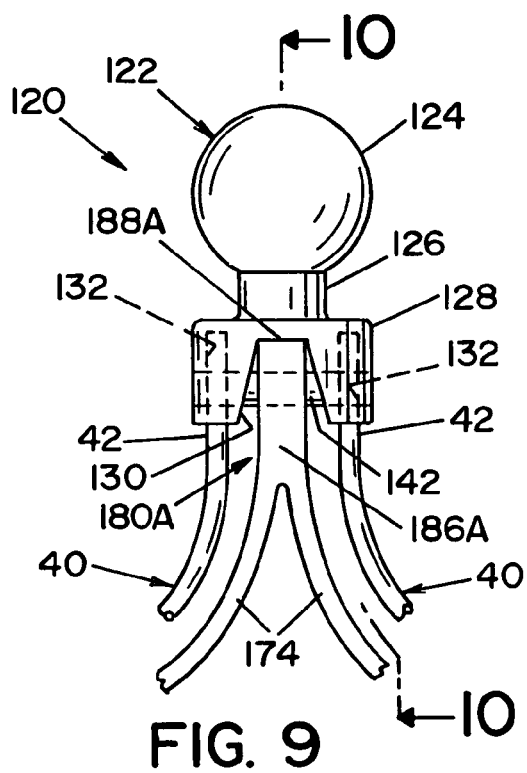
FIG. 9 is a front view of the mounting assembly and the corresponding mounting section of FIG. 8, wherein said mounting assembly and the corresponding mounting section are in engagement.
Figure 10:
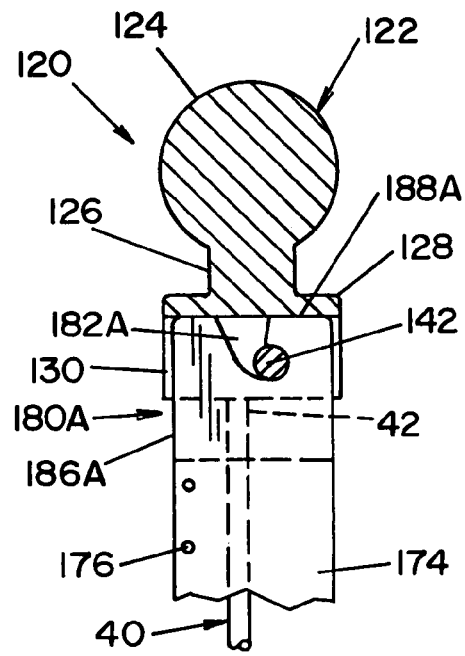
FIG. 10 is a partial cross-sectional view of the mounting assembly engaged with the corresponding mounting section, taken along lines 10-10 of FIG. 9.

FIGS. 8-10 illustrate a valve frame mounting assembly 120 and a base member mounting section 180A, according to an alternative embodiment of the present invention. In this regard, mounting assembly 120 is generally comprised of a cap 122 and a mounting element 142. In the embodiment shown, cap 122 has a bulbous portion 124, a neck 126 and a base 128. Recesses 132 are located in base 128, and are dimensioned to receive end portions 42 of adjacent wireform sections 40. A slot 130 is formed in base 128, and is dimensioned to receive a portion of mounting section 180A, as best seen in FIG. 9. Mounting element 142 takes the form of a pin or bar that extends across slot 130, as best seen in FIGS. 8 and 9.

Mounting section 180A includes a recess 182A formed in an upper face 188A. In the embodiment shown, recess 182A takes the form of a generally L-shaped slot. Recess 182A is dimensioned to receive mounting element 142 to attach mounting assembly 120 to mounting section 180A. Mounting element 142 and mounting section 180A define interlocking surface means. It should be appreciated that mounting section 180A has a relatively narrow outer face 186A.

Figure 11:
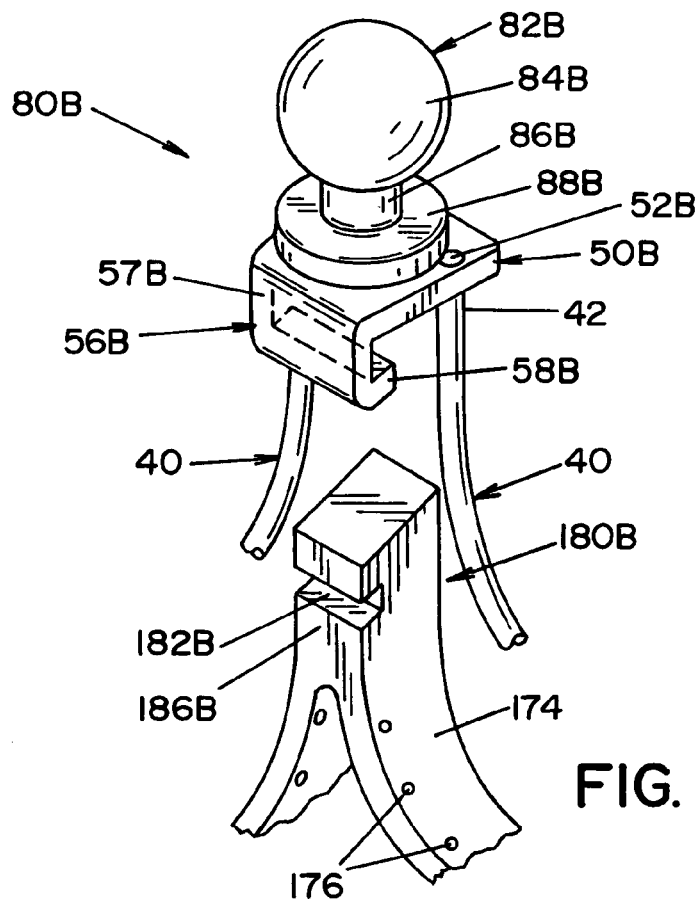
FIG. 11 is a perspective view of a mounting assembly and a corresponding mounting section, according to another alternative embodiment.
Figure 13:
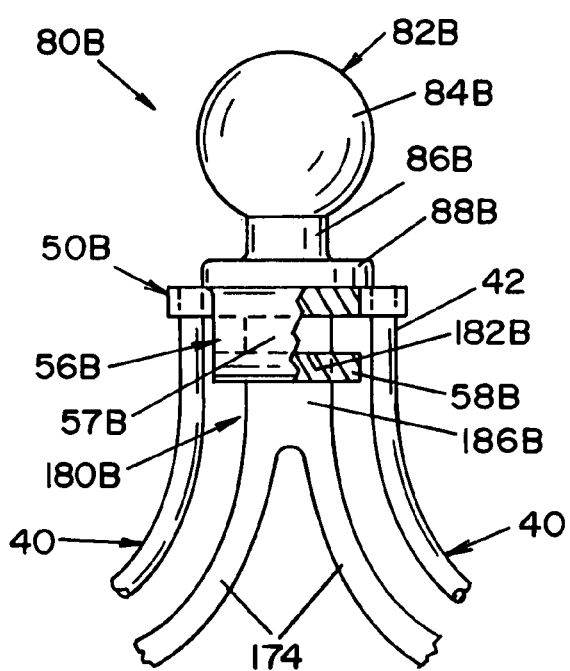
FIG. 13 is a partial cross-sectional view of the mounting assembly and the corresponding mounting section, taken along lines 13-13 of FIG. 12.
Figure 12:
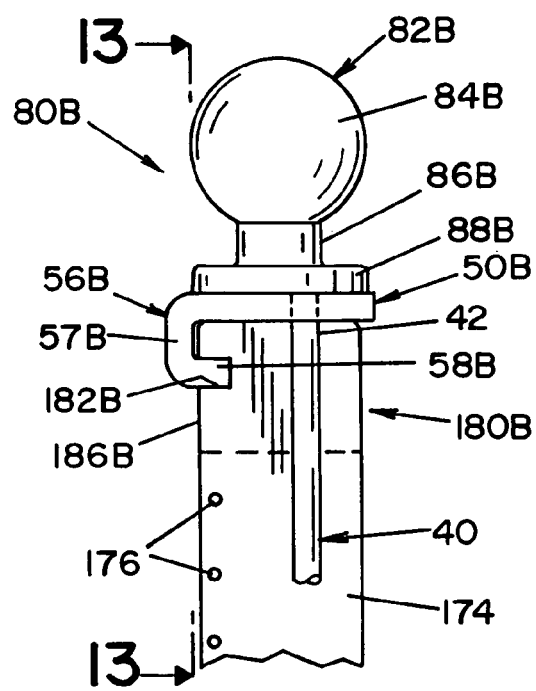
FIG. 12 is a side view of the mounting assembly and the corresponding mounting section of FIG. 11, wherein said mounting assembly and the corresponding mounting section are in engagement.

FIGS. 11-13 illustrated a valve frame mounting assembly 80B and a base member mounting section 180B according to still another alternative embodiment of the present invention. In this regard, mounting assembly 80B is comprised of a cap 82B, a plate 50B, and a mounting element 56B. Cap 82B includes a bulbous portion 84B, a neck 86B and a base 88B. By way of example, and not limitation, cap 82B may be attached to plate 50B by spot welding or by a fastener (e.g., a screw). Plate 50B includes recesses 52B that are dimensioned to receive end portions 42 of wireform sections 40. In the embodiment shown, mounting element 56B takes the form of a clip, hook, or latch member that extends from plate 50B. In this regard, mounting element 56B includes a downward extending wall 57B and an inward extending wall or tab 58B, as best seen in FIGS. 11 and 12.

Mounting section 180B has an outer face 186B and an upper face 188B. A slot or recess 182B is formed in outer face 186B. Recess 182B is dimensioned to receive inward extending tab 58B of plate 50B to attach mounting assembly 80B to mounting section 180B. Mounting element 56B and mounting section 180B define interlocking surface means. When tab 58B is received by recess 182B, the lower surface of plate 50B rests on upper face 188B. It should be appreciated that mounting section 180B has a relatively narrow outer face 186B.

Figure 14:
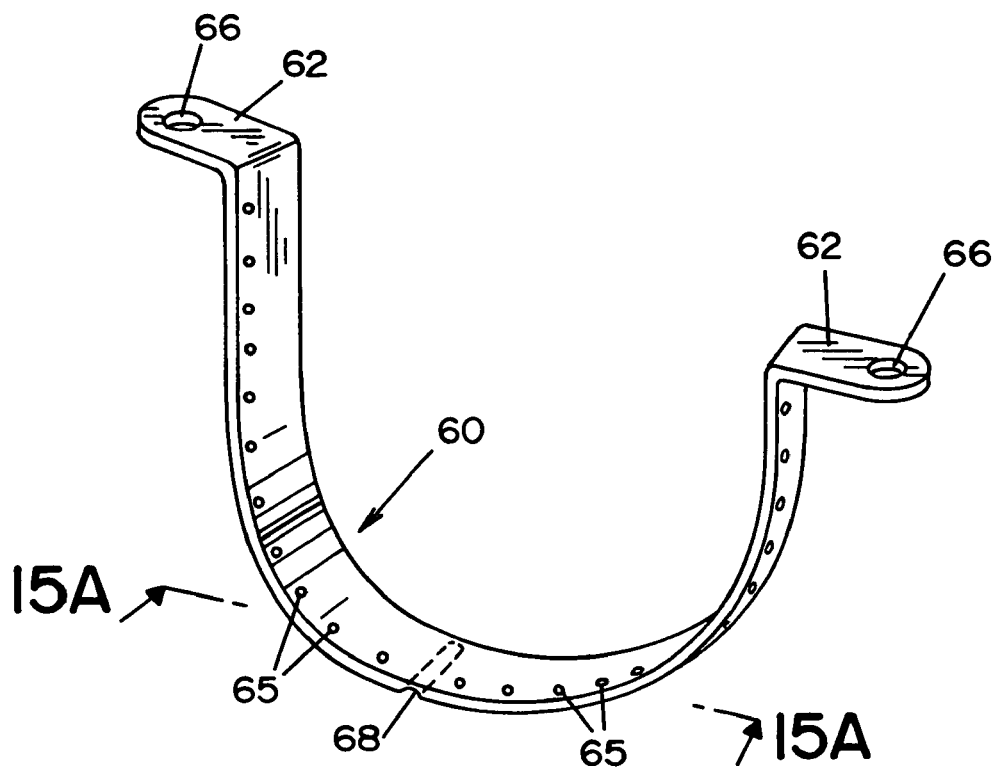
FIG. 14 is a perspective view of a hinged wireform section according to an alternative embodiment.
Figure 15A:
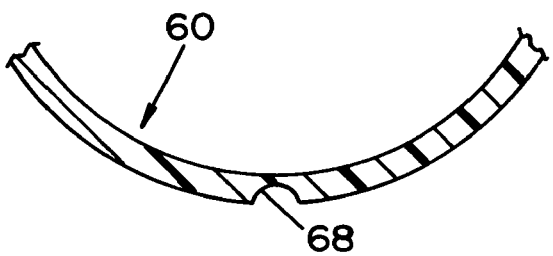
FIG. 15A is an enlarged cross-sectional view of the hinged wireform section, taken along lines 15A-15A of FIG. 14, wherein the wireform section is shown in an uncollapsed state.
Figure 15B:
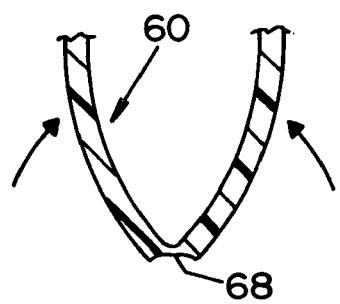
FIG. 15B is an enlarged cross-sectional view of the hinged wireform section of FIG. 15A, wherein the wireform section is shown in a collapsed state.

Referring now to FIGS. 14 and 15A-15B, there is shown an alternative embodiment for the wireform sections. Wireform section 60 is a generally flat ribbon or strip having distal end portions in the form of outward projecting mounting tabs 62. Each mounting tab 62 includes a hole 66. Hole 66 is dimensioned to receive a retaining pin for attachment with a mounting assembly, as described above. Holes 65 may be located along the length of wireform section 60 for attachment of base wraps 250 thereto by stitching. At or near the center of wireform 60, a notch 68 may be formed therein (FIG. 15A) to form a "living hinge." Notch 68 defines a hinged area of wireform 60 that allows wireform section 60 to flex, as shown in FIG. 15B. Wireform section 60 is preferably made of a medical grade polymer material, such as poly-ether-ether-ketone (PEEK), polyurethane or polycarbonate. The polymer material is preferably fabricated so as to align the molecules along a hinging axis located at notch 68.

Figure 16:
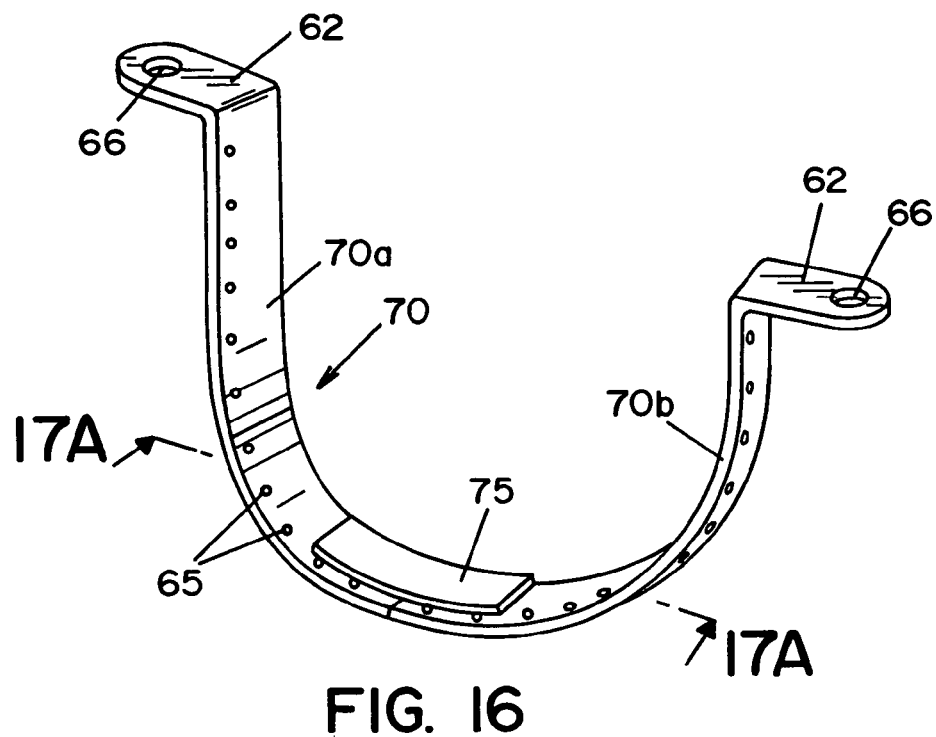
FIG. 16 is a perspective view of a hinged wireform section according to another alternative embodiment.
Figure 17A:
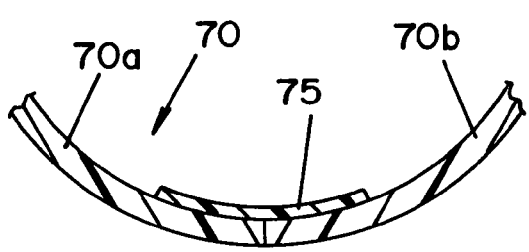
FIG. 17A is an enlarged cross-sectional view of the wireform section taken along lines 17A-17A of FIG. 8, wherein the wireform section is shown in an uncollapsed state.
Figure 17B:
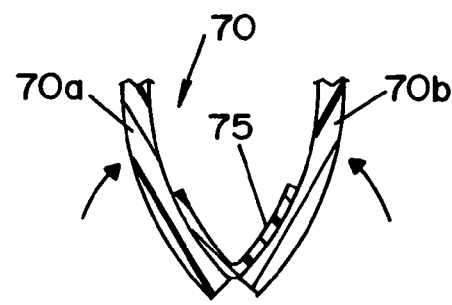
FIG. 17B is an enlarged cross-sectional view of the wireform section of FIG. 17A, wherein the wireform is shown in a collapsed state.

Referring now to FIGS. 16 and 17A-17B, there is shown another alternative embodiment of a wireform section. Like wireform section 60, wireform section 70 also takes the form of a flat ribbon or strip having distal end portions in the form of outward projecting mounting tabs 62. However, wireform section 70 is comprised of individual wireform portions 70*a* and 70*b* joined together at or near the center of wireform 70 by a connecting pad 75 (FIG. 17A). Connecting pad 75 is made of a flexible material that allows wireform portions 70*a* and 70*b* to flex relative to each other, as shown in FIG. 17B. Thus, connecting pad 75 forms a hinge for wireform portions 70*a* and 70*b*. Wireform portions 70*a* and 70*b* are preferably made of a polymer material, such as poly-ether-ether-ketone (PEEK), polyurethane or polycarbonate. Connecting pad 75 is preferably made of a polymer material, such as such as poly-ether-ether-ketone (PEEK), polyurethane or polycarbonate.

As indicated above, the wireform of the present invention may be comprised of a single continuous wireform section. In accordance with the embodiments of wireform sections 60 and 70 described above, a single continuous wireform may take the form of a flat ribbon or strip in a ring-like arrangement, wherein mounting tabs are formed in the single continuous wireform section at appropriate locations.

Assembly and operation of cardiovascular valve assembly 10 will now be described with reference to a cardiovascular valve assembly 10 according to the embodiment shown in FIGS. 1-6. It should be appreciated that operation of the cardiovascular valve assembly according to alternative embodiments described herein is substantially the same.

Beginning with initial assembly and installation of cardiovascular valve assembly 10, a plurality of frame wraps 210 and leaflets 230 are attached to valve frame 30, as described above, to form a fully assembled valve member 20. Furthermore, a plurality of base wraps 250 and sewing cuff 270 are attached to base member 170, as described above. Thereafter, assembly of cardiovascular valve assembly 10 is completed by engaging valve frame 30 with base member 170 (FIG. 1). In this regard, each mounting element 102 of mounting assemblies 80 is received into a respective mating recess 182 of mounting sections 180. When assembled, wireform sections 40 of valve frame 30 will extend generally parallel to arcuate sections 172 of base member 170. It should be understood that engagement of valve frame 30 with base member 170 may require a small temporary expansion of valve frame 30 in order to fit mounting elements 102 into respective mating recesses 182. Thereafter, fully assembled cardiovascular valve assembly 10 is sewn to a patient using sewing cuff 270.

Figure 18A:
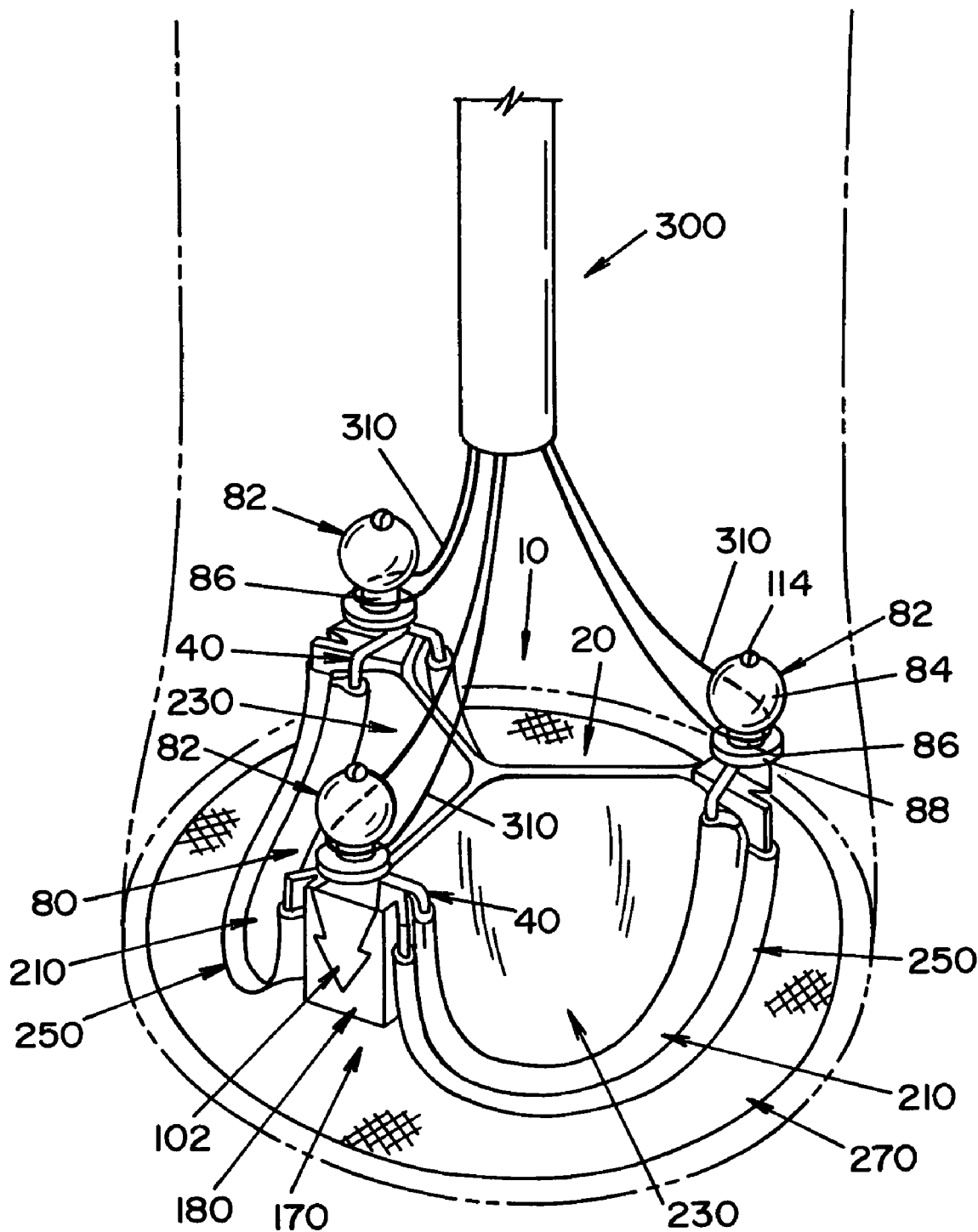
FIGS. 18A-18C illustrate removal of a valve member from a base member using an installation/removal tool.
Figure 18B:
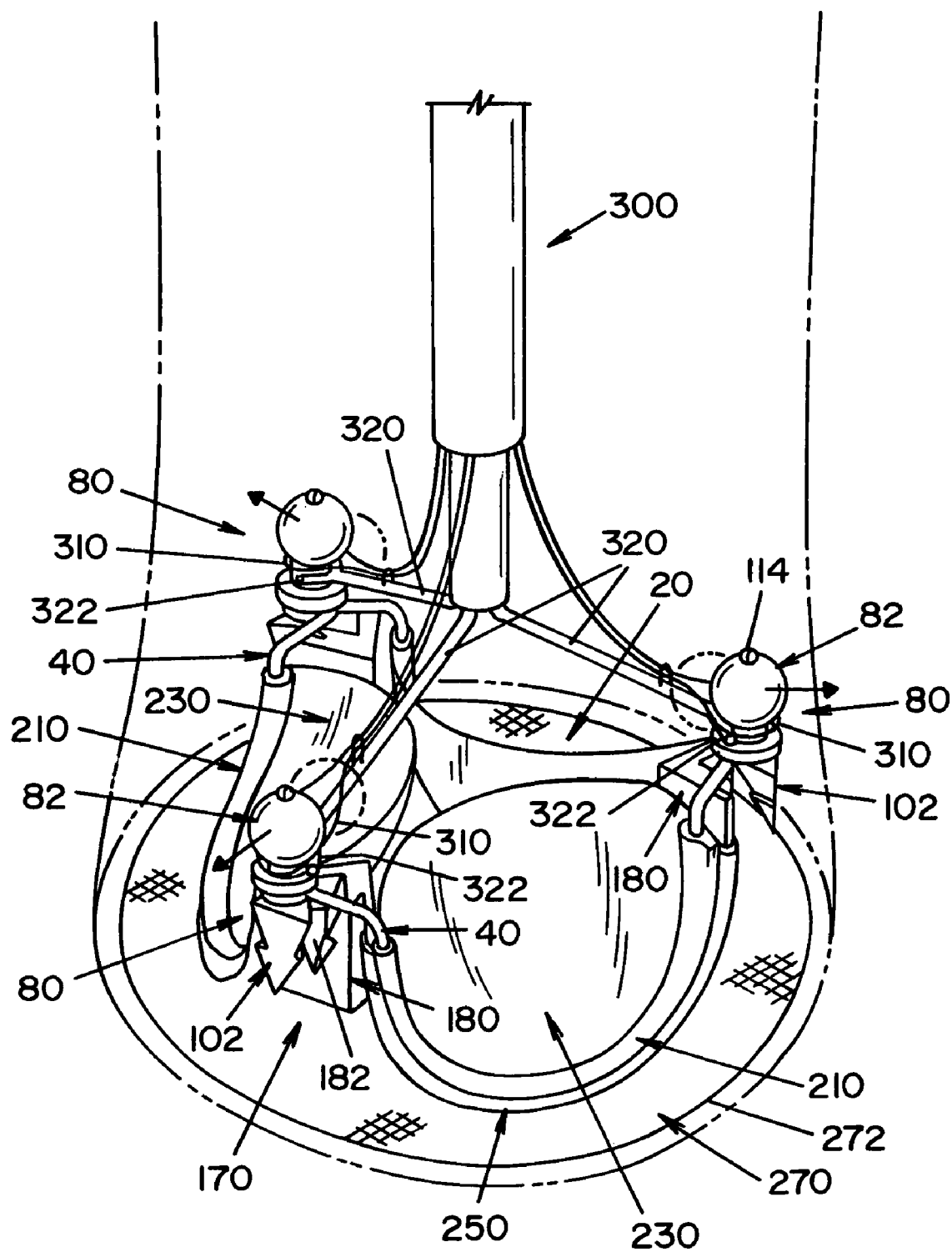
Figure 18C:
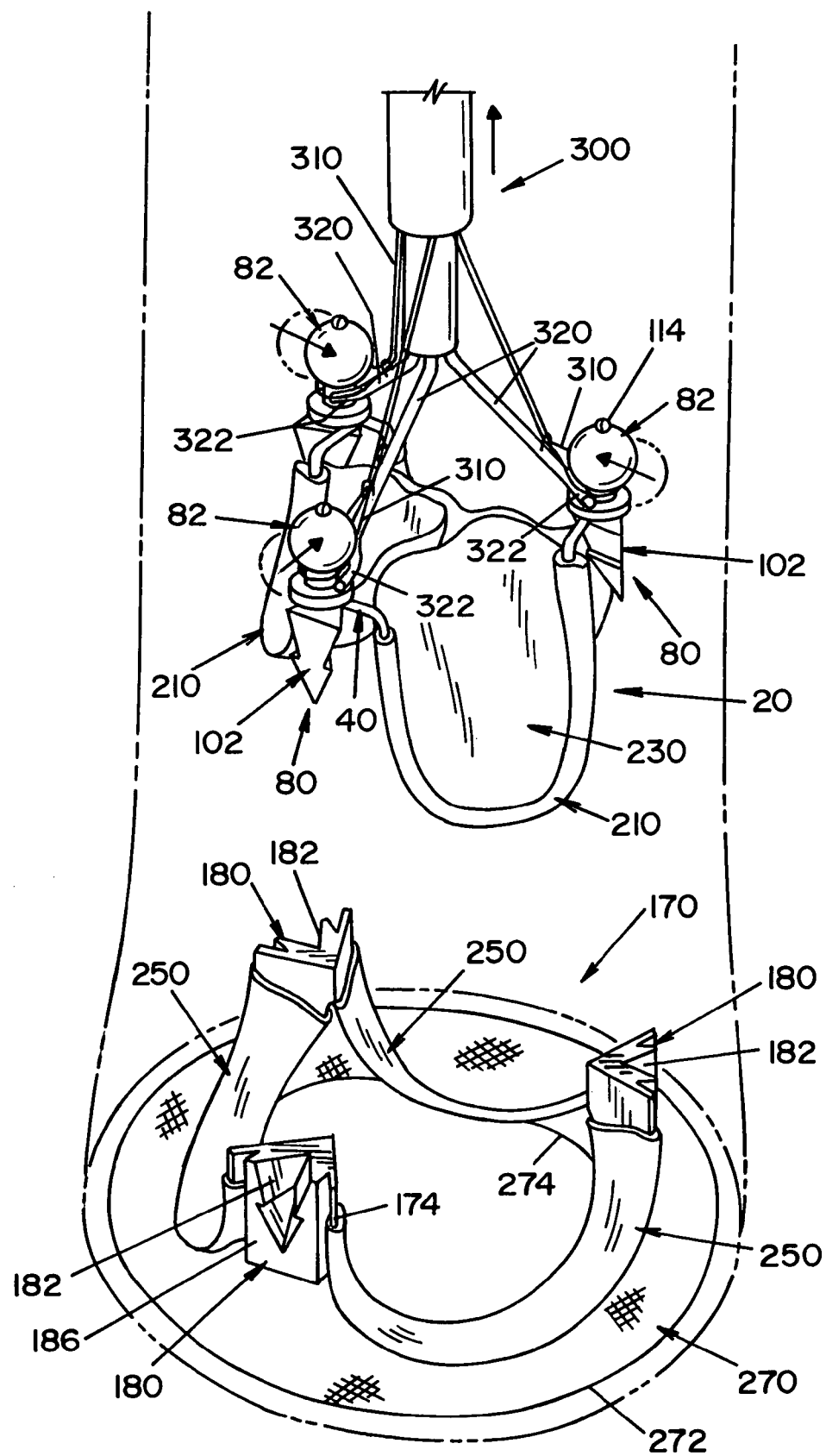

When it becomes necessary to replace valve member 20, an installation/removal tool 300 may be used (see FIGS. 18A-18C). Tool 300 includes a plurality of preformed, retractable snares 310 and a plurality of expander elements 320. In the illustrated embodiment, there are three snares 310 and three expander elements 320. However, it is contemplated that the number of snares and expander elements may vary depending upon the configuration of cardiovascular valve assembly 10. Each expanding element 320 has an engagement member 322 at a distal end thereof. Tool 300 allows for removal and insertion of valve member 20 in a simple pull-out/push-in operation that does not require visualization once tool 300 is attached to the valve member 20, as will be described below Removal of valve member 20 from base member 170 will now be described in detail with reference to FIGS. 18A-18C. To separate valve member 20 from base member 170, snares 310 are looped around necks 86 of each cap 82 (FIG. 18A). It should be appreciated that the shape and location of cap 82 allows cap 82 to be grabbed by snares 310 even if there is considerable tissue overgrowth.

Referring now to FIG. 18B, mounting elements 102 are disengaged from mounting sections 180 by engaging engagement member 322 of each expanding element 320 with neck 86 of each cap 82. Expanding elements 320 are moved from a retracted position to an expanded position to simultaneously force each mounting assembly 80 outward, thereby disengaging mounting elements 102 from mounting sections 180. As a result, valve member 20 is released from base member 170. Thereafter, valve member 20 may then be partially or fully collapsed by moving engagement members 322 from the expanded position to the retracted position, and drawing snares 310 inward, as shown in FIG. 18C. Accordingly, valve member 20 can be conveniently withdrawn from the aorta through a port access system (not shown). The port access system may take the form of a temporary Dacron graft sewn onto the vessel.

A replacement valve member 20 is installed by generally reversing the operation described above for removal.

It should be understood that valve member 20 is detachable from base member 170 by way of outward deflection of valve frame 30 at mounting assembly 80. Deflection may occur by use of installation/removal tool 300, as described above, or alternatively by a surgeon's fingers.

According to a preferred embodiment of the present invention wireform sections 40 of the valve frame 30 are made of a deformable material and/or include hinge means, as described above. However, it is also contemplated that according to an alternative embodiment of the present invention wireform sections 40 may be generally rigid (i.e., not be made of a deformable material and/or include any hinge means), and thus do not collapsible as described above.

Other modifications and alterations will occur to others upon their reading and understanding of the specification. It is intended that all such modifications and alterations be included insofar as they come within the scope of the invention as claimed or the equivalents thereof.

Having described the invention, the following is claimed:

1. A cardiovascular valve assembly having a first end and a second end, said valve assembly comprising:

a base member comprised of a plurality of arcuate base sections and a plurality of mounting sections, each arcuate base section having a pair of distal ends that are disposed closer to the first end of the valve assembly than the remainder of the arcuate base section, wherein the distal ends of adjacent arcuate base sections join a common mounting section; and a valve member detachably mountable to the base member, said valve member including:

a plurality of mounting assemblies respectively engageable with the plurality of mounting sections in an interlocking manner such that the valve member can be removed and replaced, and a plurality of arcuate portions for supporting a plurality of leaflets, each arcuate portion having a pair of distal ends, wherein respective mounting assemblies are located at distal ends of adjacent arcuate portions, wherein said plurality of arcuate portions of said valve member are respectively seated on, and extend generally parallel to, said plurality of arcuate base sections to form a seal therebetween when said plurality of mounting sections are engaged with said plurality of mounting assemblies in an interlocking manner.

2. A cardiovascular valve assembly according to claim 1, wherein said plurality of arcuate portions are comprised of a single continuous wire.

3. A cardiovascular valve assembly according to claim 1, wherein each of said plurality of arcuate portions is formed of an individual wire.

4. A cardiovascular valve assembly according to claim 1, wherein said plurality of arcuate portions are formed of a material having an elasticity such that it returns to its original shape after being deformed.

5. A cardiovascular valve assembly according to claim 1, wherein each of said plurality of arcuate portions is comprised of a generally flat ribbon formed of a polymer material.

6. A cardiovascular valve assembly according to claim 1, wherein each said arcuate portion includes at least one kink formed therein.

7. A cardiovascular valve assembly according to claim 1, wherein each said arcuate portion includes hinge means.

8. A cardiovascular valve assembly according to claim 7, wherein said hinge means includes a notch formed in said arcuate portion.

9. A cardiovascular valve assembly according to claim 7, wherein each said arcuate portion includes a first portion and a second portion, said hinge means including a flexible connecting pad that joins the first portion to the second portion.

10. A cardiovascular valve assembly according to claim 1, wherein each mounting assembly of the valve member includes a mounting element engageable with said base member to interlock the mounting assembly with a respective mounting section of the base member.

11. A cardiovascular valve assembly according to claim 10, wherein said mounting element includes a prismatic-shaped spike.

12. A cardiovascular valve assembly according to claim 10, wherein said mounting element includes a bar.

13. A cardiovascular valve assembly according to claim 10, wherein said mounting element includes a clip.

14. A cardiovascular valve assembly according to claim 10, wherein each mounting section of said base member includes at least one mating recess for respectively receiving said mounting element of each said mounting assembly.

15. A cardiovascular valve assembly according to claim 14, wherein said at least one mating recess is a slot.

16. A cardiovascular valve assembly according to claim 1, wherein each mounting assembly of the valve member includes a cap.

17. A cardiovascular valve assembly according to claim 16, wherein each mounting assembly of the valve member includes a retaining pin engageable with said cap.

18. A cardiovascular valve assembly according to claim 16, wherein said cap includes a bulbous portion.

19. A cardiovascular valve assembly according to claim 1, wherein each of said mounting sections of said base member includes a mating recess for receiving a respective mounting element of said mounting assembly.

20. A cardiovascular valve assembly according to claim 1, wherein said cardiovascular valve assembly further comprises a sewing cuff attached to said base member.

21. A cardiovascular valve assembly according to claim 1, wherein said plurality of leaflets are respectively attached to said plurality of arcuate portions of said valve member such that an edge of said plurality of leaflets extends at least 1 mm beyond said arcuate portions.

22. A cardiovascular valve assembly according to claim 1, wherein said plurality of arcuate portions are comprised of a single continuous generally flat ribbon formed of a polymer material.

23. A cardiovascular valve assembly according to claim 1, wherein each of said arcuate portions includes a plurality of holes.

24. A cardiovascular valve assembly according to claim 1, wherein each of said arcuate base sections includes a plurality of holes.

* * * * *